(12) United States Patent
Meingassner

(10) Patent No.: US 7,259,170 B2
(45) Date of Patent: Aug. 21, 2007

(54) MACROLIDES CONTAINING PHARMACEUTICAL COMPOSITIONS

(75) Inventor: Josef G Meingassner, Perchtoldsdorf (AT)

(73) Assignee: Novartis AG, Basel (CH)

( * ) Notice: Subject to any disclaimer, the term of this patent is extended or adjusted under 35 U.S.C. 154(b) by 323 days.

(21) Appl. No.: 10/492,439

(22) PCT Filed: Oct. 22, 2002

(86) PCT No.: PCT/EP02/11799

§ 371 (c)(1),
(2), (4) Date: Apr. 13, 2004

(87) PCT Pub. No.: WO03/035068

PCT Pub. Date: May 1, 2003

(65) Prior Publication Data

US 2004/0192716 A1    Sep. 30, 2004

(30) Foreign Application Priority Data

Oct. 23, 2001 (GB) ................................. 0125443.2
Nov. 14, 2001 (GB) ................................. 0127341.6

(51) Int. Cl.
*A61K 31/44* (2006.01)

(52) U.S. Cl. ........................ 514/291; 514/452; 536/6.5; 536/7.1; 536/7.2

(58) Field of Classification Search ................. 514/291, 514/63, 321, 452, 847; 540/452, 456
See application file for complete search history.

(56) References Cited

U.S. PATENT DOCUMENTS 5,482,965 A * 1/1996 Rajadhyaksha ............. 514/452
6,274,629 B1    8/2001 Cottens et al. ............. 514/646

FOREIGN PATENT DOCUMENTS

| EP | 0 349 061 | 1/1990 |
|----|-----------|--------|
| EP | 0 427 680 | 5/1991 |
| EP | 0 627 406 | 12/1994 |
| EP | 0 778 263 | 6/1997 |
| EP | 1 002 792 | 5/2000 |
| EP | 1 050 301 | 11/2000 |
| GB | 2252041   | 7/1992 |
| WO | 94/21642  | 9/1994 |
| WO | 97/14439  | 4/1997 |
| WO | 98/22100  | 5/1998 |
| WO | 01/60345  | 8/2001 |
| WO | 02/056790 | 7/2002 |

OTHER PUBLICATIONS

Dumont, "FTY-720 Novartis/Yoshitomi", Current Opinion in Anti-Inflammatory and Immunomodulatory Investigational Drugs, vol. 2, No. 4, pp. 314-331 (2000).

Fukuda et al., "Effect of FTY720 on Immunoregulation in Concordant Xenotransplantation", Transpl. Int., vol. 11, Suppl. 1, pp. S461-S464 (1998).

Furukawa et al., "Prolongation of Canine Liver Allograft Survival by a Novel Immunosuppressant, FTY720: Effect of Monotherapy and Combined Treatment with Conventional Drugs", Transplantation, vol. 69, No. 2, pp. 235-?? (2000).

Hoshino et al., "FTY720, a Novel Immunosuppressant, Shows a Synergistic Effect in Combination with FK 506 in Rat Allograft Models", Transplantation Proceedings, vol. 31, pp. 1224-1226 (1999).

Kahan et al., "Current Immunosuppressant Regimens: Considerations for Critical Care", Curr. Opin. Crit. Care, vol. 7, pp. 242-250 (2001).

Kelly et al., "Review: Metabolism of Immunosuppressant Drugs", Current Drug Metabolism, vol. 3, pp. 275-287 (2002).

Miyata et al., "Prolongation of Concordant Xenograft Survival by Treatment With FTY720", Transplantation Proceedings, vol. 30, pp. 4163-4165 (1998).

Morel, "mTOR and FTY 720 Inhibitors", Presse Med, vol. 30, No. 24, pp. 35-37 (2001)—Abstract Needed.

Nikolova et al., "Efficacy of SDZ RAD compared with CsA Monotherapy and Combined RAD/FTY720 Treatment in a Murine Cardiac Allotransplantation Model", Transplant Immunology, vol. 9, pp. 43-49 (2001).

Seiichi, "Development of Immunological Adjustment Technology for Transplantation", Kanmin Kyodo Purojekuto Kenkyu Hokoku, pp. 107-112 (1997)—JICST-EPlus Abstract No. 970791088.

Tamura, "Combination Effect of FTY720 and Tacrolimus in Rat Liver Transplantation", Keio Igaku, vol. 79, No. 2, pp. T273-T282 (2002)—HCAPLUS Abstract No. 2002:327475.

Tamura et al., "Immunosuppressive Therapy Using FTY720 Combined with Tacrolimus in Rat Liver Transplantation", Surgery, vol. 127, pp. 47-54 (2000).

Tamura et al., "Combination Effect of Tacrolimus and FTY720 in Liver Transplantation in Rats", Transplantation Proceedings, vol. 31, pp. 2785-2786 (1999).

Xu et al., "Effect of Peritransplant FTY720 Alone or in Combination with Post-Transplant Tacrolimus in a Rat Model of Cardiac Allotransplantation", Transpl. Int., vol. 11, pp. 288-294 (1998).

Xu et al., "Effect of Peritransplant FTY720 Alone or in Combination with Posttransplant FK 506 in a Rat Model of Cardiac Allotransplantation", Transplantation Proceedings, vol. 29, pp. 2964-2966 (1997).

* cited by examiner

*Primary Examiner*—Michael G. Hartley
*Assistant Examiner*—James W. Rogers
(74) *Attorney, Agent, or Firm*—Gregory C. Houghton

(57) ABSTRACT

A pharmaceutical compound comprising a compound of formula I and a pharmaceutically acceptable 2-amino-1,3-propanediol beside one or more pharmaceutically acceptable excipient(s).

4 Claims, 2 Drawing Sheets

MACROLIDES CONTAINING PHARMACEUTICAL COMPOSITIONS

The present invention relates to pharmaceutical compositions, e.g. for the treatment of pathological conditions comprising co-administration of pharmaceutically active agents. Treatment includes prevention and/or therapy.

In one aspect the present invention provides a pharmaceutically active compound of formula

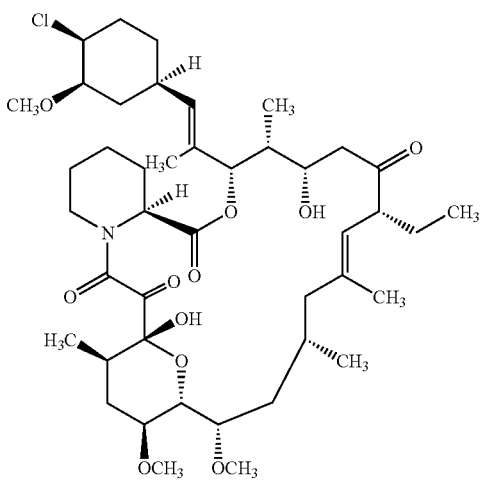

I such as disclosed in EP 427 680 (33-epi-33-chloro-FR 520 of example 66a), and a 2-amino-1,3-propanediol beside one or more pharmaceutically acceptable excipient(s).

Pharmaceutically acceptable excipient(s) e.g. includes pharmaceutically acceptable auxiliaries, carrier(s), diluent(s). A 2-amino-1,3-propanediol may comprise one or more 2-amino-1,3-propanediols.

A compound of formula I, is known to be active for the treatment of various disorders/diseases such as e.g. inflammatory conditions, immunologically-mediated disorders, or autoimmune diseases, e.g. vasculitides, glomerulonephritides, atopic dermatitis, allergies (such as allergic contact eczema, asthma), psoriasis, systemic lupus erythematodes, rheumatoid arthritis, inflammatory bowel diseases (e.g. Crohn's disease, ulcerative colitis), multiple sclerosis, insulin-dependent diabetes, Sjögren's syndrome, endogenous posterior uveitides (in particular Behcet's disease), Hashimoto's thyroititis and to prevent rejections of xenografts or allografts, e.g. including heart, renal, hepatic or bone marrow transplants; graft vessel diseases or graft vs host diseases.

A 2-amino-1,3-propanediol as referred to herein includes a compound of formula

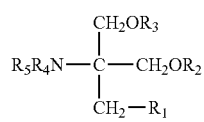

II wherein $R_1$ is an optionally substituted straight- or branched $(C_{12-22})$carbon chain, e.g. an alkyl chain, which is optionally interrupted by optionally substituted phenylene, and, independently of each other, $R_2$, $R_3$, $R_4$ and $R_5$ are H or lower alky. When the carbon chain in the meaning of $R_1$ is substituted, it is preferably substituted by halogen, nitro, amino, hydroxy or carboxy. When the carbon chain is interrupted by optionally substituted phenyl, the carbon chain is preferably unsubstituted. When the phenylene moiety is substituted, it is preferably substituted by halogen, nitro, amino, methoxy, hydroxy or carboxy. "Lower alkyl" includes $(C_{1-4})$alkyl. Such compounds are e.g. disclosed in EP627406, EP778263, EP1002792 or WO02/06268, the relevant disclosure of which, in particular with respect to the compounds, is incorporated herein by reference.

Preferred compounds include compounds of formula II, wherein $R_1$ is a straight or branched, preferably straight, $(C_{13-20})$carbon chain optionally substituted by nitro, halogen, amino, hydroxy or carboxy, and, more preferably compounds of formula II, wherein $R_1$ is phenylalkyl, optionally substituted by halogen, e.g. wherein alkyl is $(C_{1-6})$alkyl, optionally substituted by hydroxy, and wherein phenyl is substituted by straight or branched $(C_{6-14})$alkyl and optionally by halogen. More preferably, $R_1$ is phenyl$(C_{1-6})$alkyl, wherein the phenyl group is substituted by straight or branched, preferably straight, $(C_{6-14})$alkyl, such as $(C_{6-14})$ alkyl-phenyl-$(C_{1-6})$alkyl. If $R_1$ is phenylalkyl, wherein phenyl is substituted by straight or branched $(C_{6-14})$alkyl,the phenyl group may be substituted by alkyl in ortho, meta or para position, preferably in para position. Preferably each of $R_2$ to $R_5$ is H.

A pharmaceutical composition may comprise a compound of formula I and a 2-amino-propanol, e.g. one as described in EP 778263, beside one or more pharmaceutically acceptable excipient(s).

In another preferred embodiment a 2-amino-1,3,-propanediol or a 2-amino-propanol is a compound having lymphocyte homing properties. Such properties may be identified according to a test like e.g. the following: A compound to be tested or the vehicle is administered orally by gavage to rats. Tail blood for hematological monitoring is obtained on day 11 to give the baseline individual values, and at 2, 6, 24, 48 and 72 hours after application. A lymphocyte homing agent is a compound which depletes peripheral blood lymphocytes by more than 50% six hours, e.g. after administration of a dose smaller than 5 mg/kg, preferably smaller than 3 mg/kg.

A still more preferred compound of a compound of formula II is a compound of formula

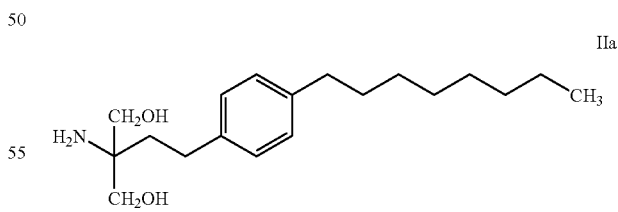

IIa e.g. 2-amino-2[2-(4-octylphenyl)ethyl]propane-1,3-diol hydrochloride. A 2-amino-1,3-propanediol, e.g. a compound of formula II, may be useful, on the basis of observed activity, e.g. as described in EP 627406, as immunomodulators, e.g. immunosuppressants, e.g. in the treatment of allograft rejections. E.g. as described in WO 98/22100, 2-amino-1,3-propanediols, e.g. of formula II, may inhibit graft vessel disease and are particularly indicated to prevent or treat chronic rejection in a transplanted organ, and additionally may suppress xenograft rejection.

According to the present invention a 2-amino-1,3-propanediol or a 2-amino-propanol is pharmaceutically active and pharmaceutically acceptable.

A compound of formula I and a 2-amino-1,3-propanediol include compounds in any form, e.g. in free form, in the form of a salt, in the form of a solvate and in the form of a salt and a solvate, where such forms exist. The compounds according to the present invention in free form may be converted into a corresponding compound in the form of a salt;

in free form or in the form of a salt and in the form of a solvate may be converted into a corresponding compound in free form or in the form of a salt in unsolvated form;

and vice versa.

The pharmaceutical activity of a compound in free form is in a similar range as that of a compound in salt/solvate form. A solvate includes a hydrate. A salt includes a pharmaceutically acceptable salt.

E.g. pharmaceutically acceptable salts of a compound of formula II include salts of a compound of formula II with an acid, e.g. including an inorganic acid, such as hydrochloric acid, hydrobromic acid and sulphuric acid, and including an organic acid, such as acetic acid, fumaric acid, maleic acid, benzoic acid, citric acid, malic acid, methanesulfonic acid and benzenesulfonic acid, and, if a carboxy group is present, salts with metals such as sodium, potassium, calcium and aluminium, amines, such as triethylamine, and dibasic amino acids, such as lysine.

In a preferred embodiment the compounds of formula II or those as described in EP1002792 includes phosphates of said compounds.

A compound of formula I and a compound of formula II may exist in isomeric forms and the present invention includes a compound of formula I and a 2-amino-1,3-propanediol according to the present invention in any isomeric form and any isomeric mixture. E.g. if a compound of formula I and a 2-amino-1,3-propanediol according to the present invention has one or more asymmetric centers in the molecule, the present invention includes the compound in the form of various optical isomers, as well as racemates, diastereoisomers and mixtures thereof.

We have now surprisingly found, that in an animal model of experimental autoimmune uveititis (EAU) wherein a compound of formula I or a 2-amino-1,3-propanediol show pharmaceutical activity, an increased activity is achieved when the compound of formula I and the 2-amino-1,3-propanediol, e.g. a compound of formula II, are co-administered in e.g. suboptimal doses. That increased activity of the co-administered compounds is remarkable higher than that of each single compound tested at the e.g. suboptimal dose level. The same principle is believed to be valid for all diseases wherein either a compound of formula I or a 2-amino-1,3-propanediol shows pharmaceutical activity, e.g. including inflammatory conditions, immunologically-mediated disorders, or autoimmune diseases, e.g. vasculitides, glomerulonephritides, atopic dermatitis,allergies (such as allergic contact eczema, asthma), psoriasis, systemic lupus erythematodes, rheumatoid arthritis, inflammatory bowel diseases (e.g. Crohn's disease, ulcerative colitis), multiple sclerosis, insulin-dependent diabetes, Sjögren's syndrome, endogenous posterior uveitides (in particular Behcet's disease), Hashimoto's thyroititis and to prevent rejections of xenografts or allografts, e.g. including heart, renal, hepatic or bone marrow transplants; graft vessel diseases or graft vs host diseases.

In another aspect the present invention provides a package comprising a compound of formula I in the form of a pharmaceutical composition beside one or more pharmaceutically acceptable excipient(s) and comprising instructions for simultaneous or sequential administration of a 2-amino-1,3-propanediol.

In another aspect the present invention provides a package comprising a 2-amino-1,3-propanediol in the form of a pharmaceutical composition beside one or more pharmaceutically acceptable excipient(s) and comprising instructions for simultaneous or sequential administration of a compound of formula I.

In another aspect the present invention provides a pharmaceutical kit, e.g. a package, comprising a compound of formula I in the form of a pharmaceutical composition beside one or more pharmaceutically acceptable excipient(s), and a 2-amino-1,3-propanediol in the form of a pharmaceutical composition beside one or more pharmaceutically acceptable excipient(s) in the same package.

In another aspect the present invention provides a method of improving the pharmaceutically activity of a compound of formula I as described earlier which method comprises co-administrating a compound of formula I and a 2-amino-1,3-propanediol to a subject in need of a treatment with a compound of formula I and/or with a 2-amino-1,3-propanediol.

The compound of formula I and a 2-amino-1,3-propanediol may be co-administrated in different ways:

a) In the form of fixed combinations, comprising a compound of formula I and a pharmaceutically active 2-amino-1,3-propanediol in the same pharmaceutical composition;

b) In the form of a (pharmaceutical) kit, in which a compound of formula I and a 2-amino-1,3-propanediol are present in the form of separate pharmaceutical compositions, sold in the same package, e.g. with instruction for co-administration;

c) In the form of free combinations, in which a compound of formula I and a 2-amino-1,3-propanediol are packaged separately, e.g. in the form of pharmaceutical compositions, wherein each of the packages include instructions for simultaneous or sequential administration.

The most efficient ratio of a compound of formula I and a 2-amino-1,3-propanediol may be dependent e.g. on the indication to be treated. Appropriate dosages and dosage ranges will of course vary depending upon, for example, the active compounds of the present invention used, the host, the mode of administration and the nature and severity of the conditions being treated. However, in general, for satisfactory results in larger mammals, for example humans, an indicated daily dosage is in the range of that which is known for a macrolactam like a pharmaceutically active compound of formula I and a pharmaceutically active 2-amino-1,3-propanediol, e.g. below these optimal dosages, administered, for example, in divided doses, e.g. up to four times a day. In general, satisfactory results are indicated to be obtained systemically at daily dosages of from about 0.5 mg/kg to about 15 mg/kg, preferably 1 mg/kg to about 15 mg/kg animal/human body weight of a compound of formula I and form about 0.005 mg/kg to 0.1 mg/kg, preferably 0.01 mg/kg to 0.1 mg/kg of a compound of formula II. Preferred ratios of compound I to II are in a range between about 3000 to 10, preferably 500 to 10.

The active compounds of the present invention may be administered by any conventional route, e.g. systemically, for example orally, e.g. in form of tablets or capsules, or parenterally, e.g. in the form of injectable solutions or suspensions; and topically, such as epicutaneous, intranasal, intratracheal administration.

In another aspect the present invention provides a method of treatment of diseases, wherein a compound of formula I and/or a 2-amino-1,3-propanediol are pharmaceutically active, e.g. including inflammatory conditions, immunologically-mediated disorders, or autoimmune diseases, e.g. vasculitides, glomerulonephritides, atopic dermatitis, allergies (such as allergic contact eczema, asthma), psoriasis, systemic lupus erythematodes, rheumatoid arthritis, inflammatory bowel diseases (e.g. Crohn's disease, ulcerative colitis), multiple sclerosis, insulin-dependent diabetes, Sjögren's syndrome, endogenous posterior uveitides (in particular Behcet's disease), Hashimoto's thyroititis and to prevent rejections of xenografts or allografts, e.g. including heart, renal, hepatic or bone marrow transplants; graft vessel dieseases or graft vs host diseases, comprising administering to a subject in need of such treatment an effective amount of a compound of formula I and a 2-amino-1,3-propanediol; e.g. in the form of

- a fixed combination, e.g. in the form of a pharmaceutical composition,
- a kit, e.g. in the form of a pharmaceutical composition of a compound of formula I and a pharmaceutical composition of a 2-amino-1,3-propanediol in the same package,
- a package comprising a compound of formula I or a 2-amino-1,3-propanediol, e.g. in the form of pharmaceutical compositions, and comprising instructions for simultaneous or sequential co-administration.

In a preferred embodiment of the present invention a compound of formula I is co-administered with a compound of formula IIa.

The compound of formula I and a 2-amino-1,3-propanediol may be administered as the sole ingredients or together with other drugs in immunomodulating regimens or other anti-inflammatory agents. For example the compounds may be used in combinations with cyclosporins, rapamycins or other ascomycins, or their immunosuppressive analogs, e.g. cyclosporin A, cyclosporin G, FK-506, rapamycin, 40-O-(2-hydroxy)ethyl-rapamycin, etc.; corticosteroids; cyclophosphamide; azathioprene; methotrexate; brequinar; leflunomide; mizoribine; mycophenolic acid; mycophenolate mofetil; 15-deoxyspergualine; immunosuppressive monoclonal antibodies, e.g. monoclonal antibodies to leukocyte receptors, e.g. to MHC, CD2, CD3, CD4, CD7, CD25, CD28, B7, CD40, CD45 or CD58 or to their ligands; or other immunomodulatory compounds, e.g. CTLA4-Ig.

Tests for the determination of the activity of a compound of formula I and 2-amino-1,3-propanediols are known. A model of experimental autoimmune uveitis (EAU) as described e.g. in *Clin. Immunol. Immunopathol.* 1986; 39: 329-336, McAllister et al.(1986) can be used.

In another aspect the present invention provides the use of a compound of formula I together with a 2-amino-1,3-propanediol, e.g. administered either simultaneously or sequentially, as a pharmaceutical; and the use of a combination of a compound of formula I and a 2-amino-1,3-propanediol in the preparation of a medicament for the treatment of diseases, wherein the compound of formula I or a 2-amino-1,3-propanediol are pharmaceutically active. Treatment includes prevention and/or therapy.

The weights in mg are indicated in mg/kg body weight/day. The means of scores of both eye lesions were determined as described in the examples within 20 days after immunization.

Figure 2:
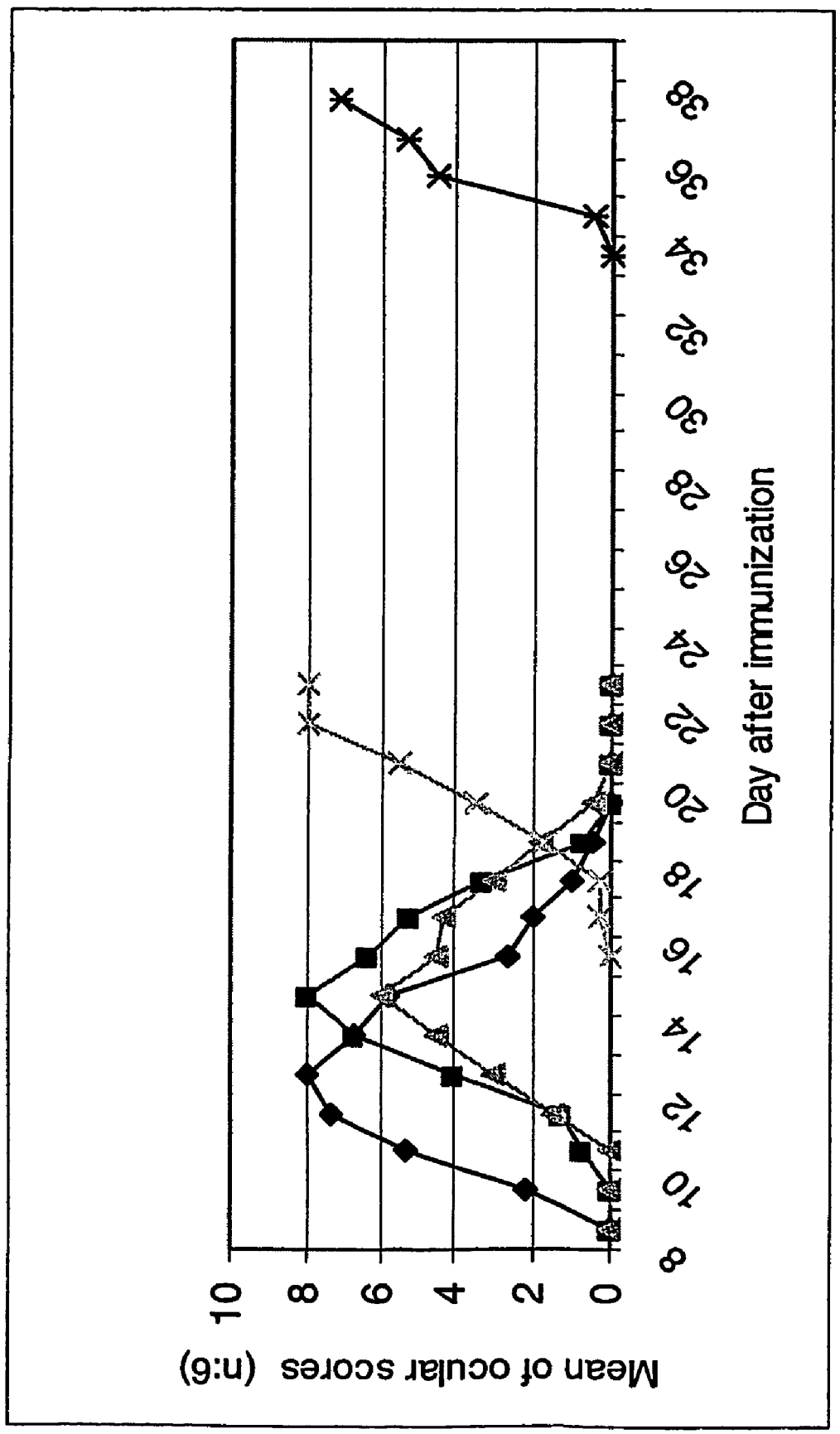

In FIG. 2, results of the Experimental autoimmune uveitits (EAU) test in rats are indicated. The rats were treated orally, once daily, for 14 days, either with
♦-: Control (placebo, i.e. drug vehicle/water),
■-: Compound of formula IIa (0.1 mg),
▲-: Compound of formula I (15 mg),
✣-: Compound of formula I (15 mg)+Compound of formula IIa (0.1 mg), 14 days, or
*-: Compound of formula I (15 mg)+Compound of formula IIa (0.1 mg), 28 days.

Figure 1:
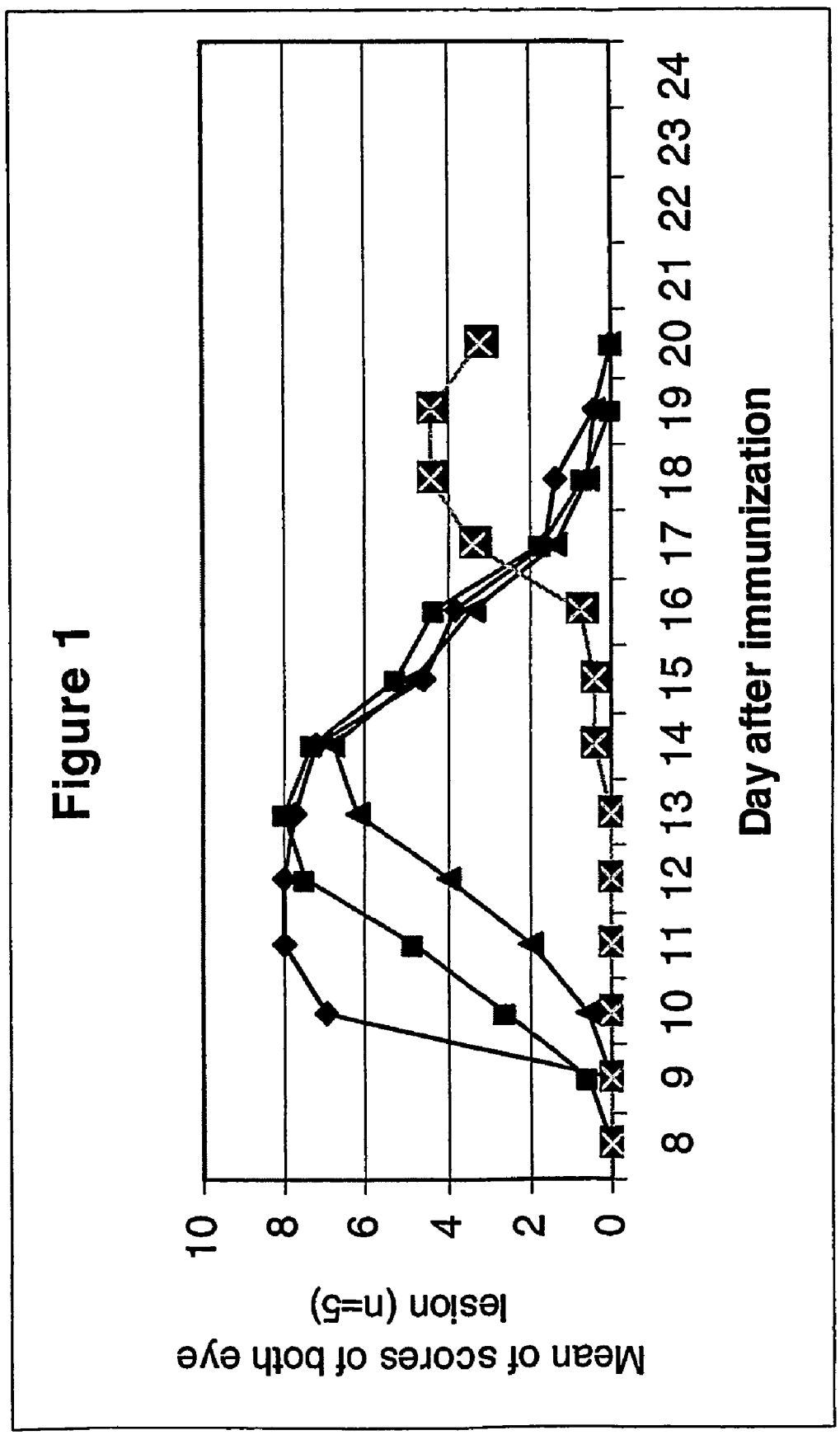
In FIG. 1, results of the Experimental autoimmune uveitits (EAU) test in rats are indicated. The rats were treated orally, once daily, for 14 days, either with
♦-: Control (placebo, i.e. drug vehicle/water),
■-: Compound of formula IIa (0.1 mg),
▲-: Compound of formula I (15 mg), or
✣-: Compound of formula IIa (1.0 mg)+Compound of formula I (15 mg).

Other parameters are as described for FIG. 1.

EXAMPLES

Example 1

EAU Test System

Experimental Autoimmune Uveitits (EAU)

The model of EAU used, is similar to that described previously by McAllister et al.(1986) (McAllister C G, Vistica B P, Sekura R, Kuwabara T, Gery I. *The effects of pertussis toxin on the induction and transfer of experimental autoimmune uveoretinitis. Clin Immunol Immunopathol* 1986; 39: 329-336). The animals (5 rats per group) are injected under ether anesthesia into the right foodpat with 50 μg of purified bovine retinal S-antigen and with 1 μg pertussis toxin (Difco) intra peritoneally on day 1. The antigen is diluted with phosphate-buffered saline and mixed 1:1 (v/v) with Freund's complete adjuvant and Bacto M Tuberculosis H37 RA (Difco). The volume injected is 0.1 ml, containing 50 μl complete adjuvant and 1.14 mg of *Mycrobacterium tuberculosis*. This procedure induces a fulimant disease in all animals which is observed earliest 9-10 days after immunisation. The eye lesions in untreated animals develop in almost all animals to severity grade 4 (see section "Evaluation of EAU").

Treatment, Dosages

The animals are treated by gavage with daily dosages of 15 mg/kg of a compound of formula I or 0.1 mg/kg of a compound of formula IIa alone; or with a combination of both compounds at the same dosage levels. The treatment is started 2 hours before immunisation and performed once daily on 14 consecutive days. Control animals are treated similarly with placebo/water alone (placebo: drug vehicle alone).

Evaluation of EAU

Starting on day 7 after immunisation the animals are examined with an ophthalmoscope (Heine, Beta 200) for inflammatory changes daily up to day 20. The extent of ocular inflammation is semi-quantitatively assessed with scores from 0 to 4 (for 1 eye).

0: normal;
1: iris hyperemia;
2: iris hyperemia with vascular dilatation;
3: early fibrinous exudate in the anterior chamber and moderate iris cell infiltration; and
4: large fibrin clot in anterior chamber or fibrin plugging of the pupil and severe iris cell infiltration.

Results

Animals (LEWIS rats) are treated orally either with 0.1 mg/kg of a compound of formula IIa or 15 mg/kg/day of a compound of formula I are not distinctively different from placebo controls in the course and intensity of the disease (see e.g. TABLE 1 and FIG. 1). In contrast, the administration of both compounds at the same dosage levels causes a remarkably delay in onset of the disease (6 days later than in controls) and the intensity of the inflammation is remarkably less. The highest mean score of treated animals is 4.4 on day 19 compared with 8.0 on day 11 in controls.

TABLE 1

| | | EAU | | | SCORE MAX | |
|---|---|---|---|---|---|---|
| Test group | Dosis | POS | EAU 10 | EAU 1st | SCORE | DAY |
| Controls | 0.0 | 5/5 | 5/5 | 10.0 (0.0) | 8.0 (0.0) | 11 |
| Cpd IIa | 0.1 | 4/4*) | 2/5 | 10.5 (0.6) | 8.0 (0.0) | 13 |
| Cpd I | 15 | 5/5 | 1/5 | 11.8 (1.3) | 6.8 (1.3) | 14 |
| Cpd IIa + Cpd I | 1.5 + 15 | 4/5 | 0/5 | 16 (1.4) | 4.4 (3.3) | 19 |

*)one animal lost on day 11 due to traumatic gavage

In TABLE 1 under "EAU POS" and "EAU 10" the number of affected animals/number of animals per group until end of the study (EAU POS), and on day 10 (EAU 10), respectively are indicated. The following abbreviations are used:
Cpd I: Compound of formula I
Cpd IIa: Compound of formula IIa
Controls: Placebo (drug vehicles/water)
Dosis: oral, in mg/kg/day
EAU POS: Number of EAU positive rats
EAU 10: Incidence of EAU on day 10
EAU 1st: Day of first signs of EAU (mean±SD)
SCORE MAX: Maximum score (mean of both eye lesions±SD)

The results from the EAU-test (used as an assay example) indicate that the combination of a suboptimal dosage of a compound of formula I plus a suboptimal dosage of a compound of formula IIa is significantly superior in activity against EAU, than the use of a suboptimal dosage of a compound of formula I, or of a suboptimal dosage of a compound of formula IIa, respectively, alone (Table 1 and FIG. 1). That effect allows the use of a suboptimal dosage of a compound of formula I plus a suboptimal dosage of a compound of formula IIa.

Example 2

Animals (6 rates per group) were treated as described in example 1 with the doses given in table 2. As depicted in table 2 and FIG. 2 the combination treatment shows superior results over the treatment with single compounds. From the animal treated on 14 days with both compounds, the first clinical signs were observed in one animal on day 16. Complete suppression of symptoms was observed also during the 4-week treatment period. Symptoms appeared earliest in one animal on day 34, 6 days after the last treatment.

TABLE 2

| | | EAU | | | SCORE MAX | |
|---|---|---|---|---|---|---|
| Test group | Dosis | POS | EAU 10 | EAU 1st | SCORE | DAY |
| Controls | — | 6/6 | 6/6 | 9.3 (0.5) | 8.0 (0.0) | 12 |
| Cpd IIa | 0.1 | 6/6 | 0/6 | 11.2 (1.0) | 8.0 (0.0) | 14 |
| Cpd I | 15 | 6/6 | 2/6 | 11.5 (0.8) | 6.0 (2.5) | 14 |
| Cpd I + Cpd IIa | 15 + 0.1 (14×) | 6/6 | 0/6 | 18.0 (1.1) | 8.0 (0.0) | 21 |
| Cpd I + Cpd IIa | 15 + 0.1 (28×) | 6/6 | 0/6 | 34.8 (0.4) | 7.2 (1.3) | 37 |

The meanings are as in legend to table 1

The results from the EAU-test (used as an assay example) indicate that the development of the disease can be prevented when treatment is performed for 4 weeks starting at immunization with a combination of compounds I and IIa.

The invention claimed is:

1. A pharmaceutical composition comprising a compound of formula

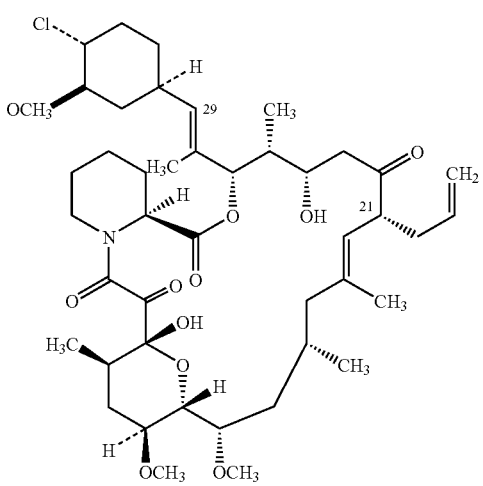

and the 2-amino-1,3-propanediol

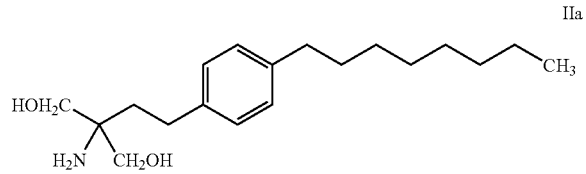

and one or more pharmaceutically acceptable excipient(s).

2. A pharmaceutical kit comprising a pharmaceutical composition according to claim 1.

3. A method of improving the pharmaceutical activity of a compound of formula I and of the pharmaceutically acceptable 2-amino-1,3-propanediol of formula IIa wherein said method comprises co-administrating a compound of formula I and the 2-amino-1,3-propanediol of formula IIa to a subject in need of treatment for inflammatory conditions, immunologically-mediated disorders or autoimmune diseases.

4. A method of treating inflammatory conditions, immunologically-mediated disorders or autoimmune diseases wherein said method a comprises administering to a subject in need of such treatment an effective amount of a pharmaceutical composition according to claim 1.

* * * * *